United States Patent
Ausherman et al.

Patent Number: 5,360,416
Date of Patent: Nov. 1, 1994

[54] THIN-WALLED ANESTHESIA NEEDLES

[75] Inventors: Ronald Ausherman, Orange City, Fla.; Thomas Heubel, Chesterfield; Michael H. Snyderman, Ballwin, both of Mo.

[73] Assignee: Sherwood Medical Company, St. Louis, Mo.

[21] Appl. No.: 129,918

[22] Filed: Sep. 30, 1993

[51] Int. Cl.$^5$ ................................ A61M 5/32
[52] U.S. Cl. ................ 604/272; 604/264; 604/158
[58] Field of Search ........... 604/272, 274, 264, 158, 604/51, 52, 53, 164

[56] References Cited

U.S. PATENT DOCUMENTS

| | | | |
|---|---|---|---|
| 2,634,726 | 4/1953 | Hanson | 128/221 |
| 2,717,600 | 9/1955 | Huber | 128/221 |
| 2,862,495 | 12/1958 | Gewecke | 128/221 |
| 3,007,471 | 11/1961 | McClure, Jr. | 128/2 |
| 3,181,336 | 5/1965 | Schofield | 72/340 |
| 4,411,657 | 10/1983 | Galindo | 604/274 |
| 4,413,993 | 11/1983 | Guttman | 604/274 |
| 4,552,554 | 11/1985 | Gould et al. | 604/51 |
| 4,645,491 | 2/1987 | Evans | 604/158 |
| 4,769,005 | 9/1988 | Ginsburg et al. | 604/53 |
| 4,808,170 | 2/1989 | Thornton et al. | 604/274 |
| 4,838,877 | 6/1989 | Massau | 604/272 |
| 4,842,585 | 6/1989 | Witt | 604/158 |
| 5,100,390 | 3/1992 | Lubeck et al. | 604/274 |
| 5,254,106 | 10/1993 | Feaster | 604/272 |

FOREIGN PATENT DOCUMENTS

| | | | |
|---|---|---|---|
| 3020926 | 12/1981 | Germany | 604/274 |
| 3022193 | 12/1981 | Germany | 604/274 |
| 897224 | 1/1982 | U.S.S.R. | 604/158 |
| 9001349 | 2/1990 | WIPO | 604/272 |

*Primary Examiner*—John G. Weiss
*Attorney, Agent, or Firm*—Andrew J. Beck; Montgomery W. Smith; Gene B. Kartchner

[57] ABSTRACT

Thin-walled anesthesia needles are disclosed which include blunted pencil point tips and each contains a built in mechanism for directing the motion of a catheter through a side opening in the needle wall for positive location of a catheter in a patient for the delivery of required medications, or for directing the flow of directly injected medications perpendicularly to the axis of the needle.

8 Claims, 2 Drawing Sheets

THIN-WALLED ANESTHESIA NEEDLES

BACKGROUND OF THE INVENTION

1. Field of the Invention

The present invention relates to needles used to deliver fluids to the body. More particularly, the present invention relates to anesthesia needles having side openings for directing fluid flow perpendicular to the axis of the needle, or for directing a catheter from the lumen of the needle out of the side opening for positive location of the catheter within a patient.

2. Prior Art

The use of rotationally symmetrical blunted needle tips, often referred to as "pencil point" tips on anesthesia needles having side openings therein for use in delivering peridural anesthesia to a patient is well known. This type of needle, when used for spinal and peridural anesthesia tends to reduce post spinal headaches and temporary or persistent neuronal losses by the patient.

U.S. Pat. No. 4,842,585 to Witt entitled "Steel Cannula for Spinal and Peridural Anesthesia", is exemplary of anesthesia needle of the type described above. The anesthesia needle of Witt includes an atraumatically pointed tip and a side opening directly adjacent thereto which allows a direct injection of liquids, or alternatively, the passage of a catheter for placement in the body. The side opening of the anesthesia needle is ground therein to form a relatively oval shaped opening into the needle lumen, with the width of the side opening being ground to correspond substantially to the diameter of the needle lumen. The distal end of the needle lumen extends beyond the ground side opening and is filled with a plug of material. The plug is positioned in the distal end of the lumen to form a guide surface across the distal end of the lumen toward the side opening. The guide surface operates to guide injection fluid or a catheter through the side opening and out of the needle.

Although the Witt needle operates adequately to guide fluid or a catheter out of the side opening thereof, there are nevertheless certain drawbacks associated with its manufacture and use. For example, the multistep manufacturing process which includes grinding the side opening and subsequently plugging the distal end of the lumen beyond the side opening, is somewhat involved. Further, since the plug used to fill the distal end of the lumen must be shaped to form a guiding surface for directing the injection fluid or the catheter through the side opening, added manufacturing difficulties also arise.

There therefore exists a need in the art to develop an anesthesia needle having a side opening therein which is simple to manufacture. There is further a need in the art to develop a guiding mechanism adjacent to the side opening which is also simple to manufacture yet is effective in guiding fluid or a catheter from the needle lumen through the side opening of the needle.

OBJECTS AND SUMMARY OF THE INVENTION

The primary object of the present invention is to develop an anesthesia needle which includes a needle point tip having a side opening adjacent thereto and a guiding mechanism for guiding fluid or a catheter from the lumen through the side opening.

It is another object of the present invention to develop an anesthesia needle in which the formation of the side opening thereof and the formation of the guiding mechanism between the side opening and the needle lumen are both formed in a single procedure.

It is further an object of the present invention to develop an anesthesia needle in which the side opening and guiding mechanism are formed without adding plugging material to the needle lumen during the manufacturing process.

These and other objects of the present invention are realized in three separate embodiments thereof in which an anesthesia needle is formed of a thin-walled metal tube having a lumen along the entire longitudinal axis thereof. The tube is swagged at the distal end thereof to form a "pencil point" tip for atraumatic insertion of the needle into a patient. A side opening is formed adjacent the tip entirely within the cylindrical portion of the needle and is formed in a generally rectangular shape as opposed to the oval shape of the prior art. The side opening is formed by making two parallel longitudinal cuts and a single perpendicular cut connecting the proximal end of the longitudinal cuts through the side wall of the tube. The cuts extend completely through the side wall into the lumen. The distal end of the parallel longitudinal cuts is directly adjacent the pencil pointed tip of the needle. The two parallel longitudinal cuts and the proximal perpendicular cut form a generally rectangular tab which is subsequently forced into the lumen to abut against the lumen wall opposite the opening. If desired, a second embodiment of the needle may also include a detent in the lumen wall directly adjacent the tab position thereagainst. In a third embodiment of the needle, the tab may be completely removed from the rectangular side opening leaving only the detent in the opposing lumen wall.

Details of the structure and use of the present invention will become more apparent from the following detailed description and the accompanying drawings in which like elements are identified with like numerals throughout.

DETAILED DESCRIPTION OF THE PREFERRED EMBODIMENTS

As shown in the exemplary drawings for the purposes of illustration, the first embodiment of a thin-walled needle made in accordance with the principles of the present invention, referred to generally by the numeral 10, is provided for placement of anesthesia medication or a catheter into a patient for spinal or peridural anesthesia.

Figure 1:
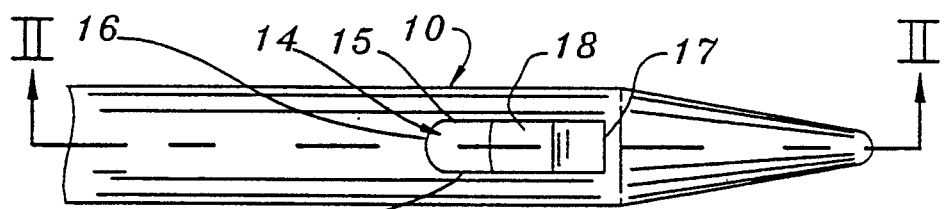
FIG. 1 is a side view of a first embodiment of a thin-walled anesthesia needle formed in accordance with the principles of the present invention.
Figure 2:
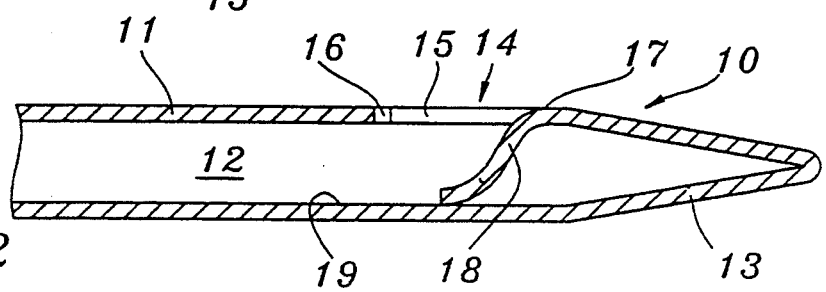
FIG. 2 is a cross-sectional view of the anesthesia needle of FIG. 1 taken along line II—II.

As shown in FIGS. 1 and 2, the needle 10 is fabricated from a thin-walled metal tube 11 formed preferably of stainless steel. The tube 11 forms a lumen 12 along the longitudinal axis thereof which extends into the tip 13. The tip 13 is formed, such as by swagging, into a blunted atraumatic rotationally symmetrical conically shaped point which is integrally formed with the tube 11. If desired, the tip 13 can alternatively be formed to a slightly spherical shape as opposed to the conical shape as shown.

Spaced directly behind the tip 13 and adjacent thereto is a generally rectangularly shaped side opening 14 which passes through the tube 11. The side opening 14 is formed with a pair of parallel longitudinally extending sides 15, a slightly curved proximal side 16, and a distal side 17 from which a tab 18 extends into the lumen 12 to contact the inside wall of the lumen 12 opposite the side opening 14.

The side opening 14 and the tab 18 are formed in a single manufacturing procedure which includes cutting the tube 11 along the parallel longitudinal sides 15 and proximal side 16 entirely through the lumen 12, and then bending the resultant tab 18 into the lumen 12 until it is forced into abutting relationship with the inside wall 19 thereof. The distance between the two parallel longitudinal sides 15 is predetermined to be of a width slightly greater than the diameter of the catheter intended to be used with the needle 10 (see catheter 40 in FIG. 7). The width of the opening 14 is at the same time sized to be of a smaller width than the diameter of the lumen 12. In this manner, fluid in lumen 12 can pass beyond the tab 18 to the extreme distal end of the needle 10, without being completely obstructed from doing so. In other words, the tab 18 does not function as a plug for the distal end of the lumen 12.

Figure 3:
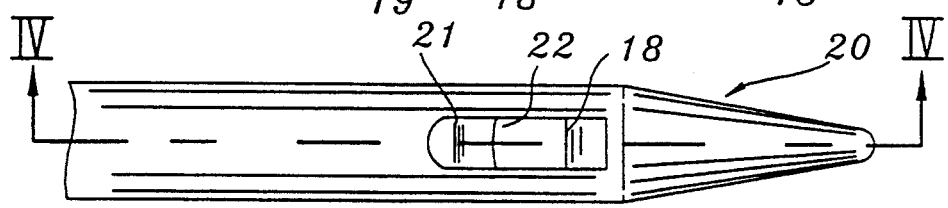
FIG. 3 is a side view of a second embodiment of a thin-walled anesthesia needle formed in accordance with the principles of the present invention.
Figure 4:
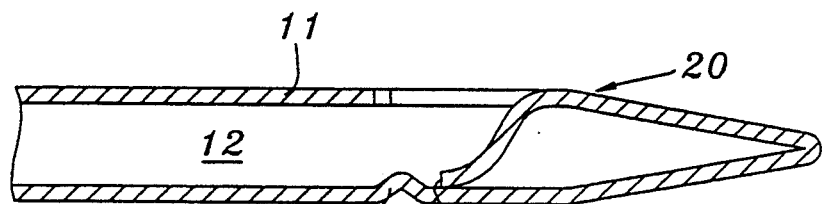
FIG. 4 is a cross-sectional view of the needle of FIG. 3 taken along line IV—IV.

Referring now to FIGS. 3 and 4, an anesthesia needle 20 is shown which is identical to the anesthesia needle 10 described above with respect to FIGS. 1 and 2 except for the additional feature of detent 21 positioned in the tube 11 so as to be adjacent the proximal end 22 of tab 18. The detent 21 is preferably raised above the surface of the inside wall 19 of a distance approximately equal to the thickness of the tab 18 in this embodiment of the invention. The detent 21 is positioned so as to shield the proximal end 22 of the tab 18 from contact with a catheter moving through the lumen 12 (refer to FIG. 8).

Figure 5:
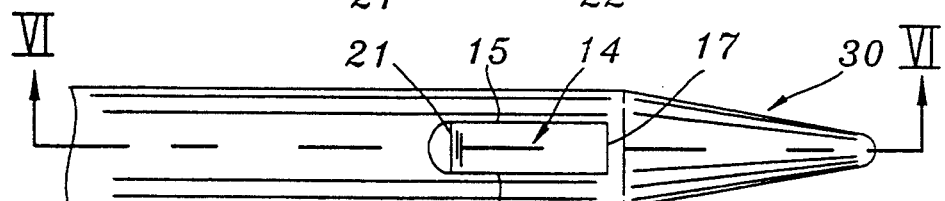
FIG. 5 is a side view of a third embodiment of a thin-walled anesthesia needle formed in accordance with the principles of the present invention.
Figure 6:
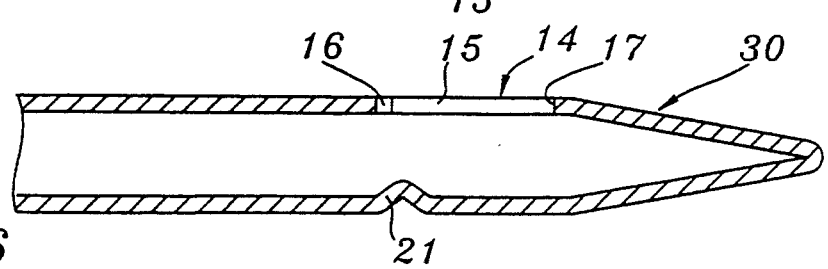
FIG. 6 is a cross-sectional view of the anesthesia needle of FIG. 5 taken along line VI—VI.

A third embodiment of the present invention is shown in the anesthesia needle 30 of FIGS. 5 and 6. Needle 30 is identical to needle 20 as shown in FIGS. 3 and 4 except that the tab 18 has been removed by cutting the tab 18 away from the distal side 17 of the side opening 14.

Figure 7:
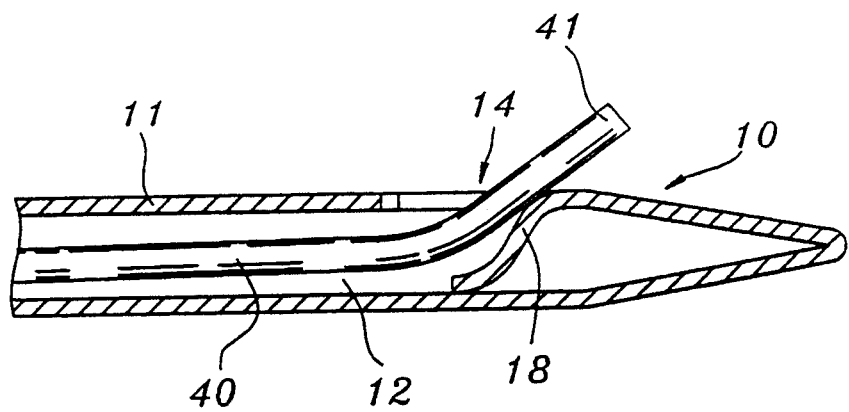
FIG. 7 is a cross-sectional view of the anesthesia needle shown in FIG. 2 with the addition of a catheter passing through the side opening thereof.

With reference to FIG. 7, the needle 10 of the present invention operates to direct a catheter 40 through the side opening 14 thereof in the manner shown. Specifically, the distal end 41 of the catheter 40 is forced down the lumen 12 until it abuts with the tab 18. Further force exerted on the catheter 40 causes the distal end 41 thereof to deflect through the side opening 14. Since the side opening 14 is generally rectangular in shape (see FIG. 1) the catheter 40 has little or no room to move laterally in the opening 14 and therefore is easier to position in a desired location by the anesthesiologist than when a needle having an ovally shaped side opening is used. Further, since the side opening 14 is formed of a width which is smaller than the diameter of the lumen 12, it does not tend to have a weakened needle tip 13 and is less likely therefor to fail such as by kinking when it is being inserted into position within a patient.

Figure 8:
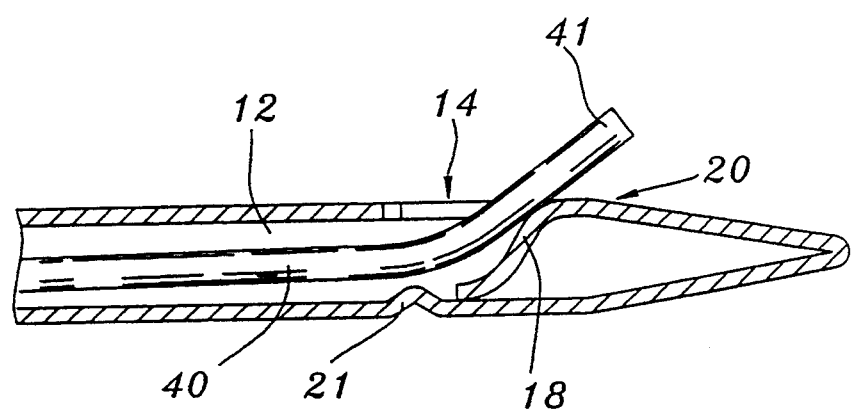
FIG. 8 is a cross-sectional view of the anesthesia needle shown in FIG. 4 with the addition of a catheter passing through the side opening thereof.

Referring now to FIG. 8, when a catheter 40 is moved through the lumen 12 of the needle 20, the distal end 41 thereof first contacts the detent 21 which causes an initial deflection of the catheter distal end 41 toward the side opening 14. Further movement of the catheter 40 down the lumen 12 causes the distal end 41 to move past the tab 18 and out of the side opening 14.

Figure 9:
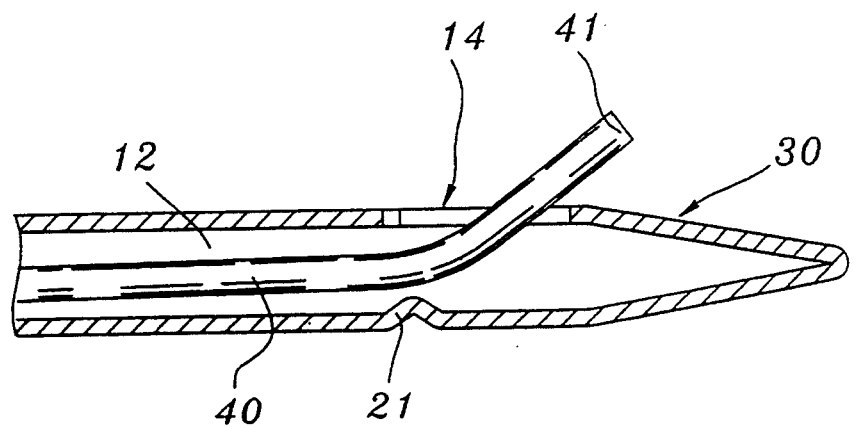
FIG. 9 is a cross-sectional view of the anesthesia needle shown in FIG. 6 with the addition of a catheter passing through the side opening thereof.

As shown in FIG. 9, a third embodiment of the invention is shown with the catheter 40. In this embodiment, the catheter 40 is initially deflected by the detent 21 a sufficient lateral distance to allow the distal end 41 to pass out of the side opening 14 as the catheter 40 continues to move down the lumen 12. As is evident, the height of the detent 21 in this embodiment of the invention may need to be adjusted depending on the particular flexibility characteristics of the catheter 40, in order to ensure that the distal end 41 thereof is sufficiently deflected to pass through the side opening 14. In this respect, the height of the detent 21 is limited only by the need to allow the lumen 12 to remain of a sufficient diameter at the point of the detent 21 for passage of the catheter 40. In other words, the restricted diameter of the lumen 12 caused by the detent 21 must be at least slightly greater than the diameter of the catheter 40.

When it is desired to inject fluids through the anesthesia needle 10, 20 or 30 of the present invention, the fluid, due to deflection by either the tab or the detent 21 or both, and due to pressurization within the lumen 12, will be forced out of side opening 14 at an angle approximately perpendicular to the longitudinal axis of the lumen 12.

It will be apparent from the foregoing, that while particular embodiments of the invention have been illustrated and described, various modifications can be made thereto without departing from the spirit and scope of the present invention. Accordingly, it is not intended that the invention be limited, except as by the appended claims.

We claim:

1. A needle comprising:
    a tube having a longitudinal axis and forming a lumen therethrough along said longitudinal axis, said tube forming a rotationally symmetrical tip at a distal end thereof and including a generally rectangular side opening adjacent said tip which extends into said lumen,
    a generally rectangular tab member integrally formed with said tube and of the same dimensions as said generally rectangular side opening extending from said side opening into said lumen and abutting an interior wall of said lumen at a position opposite said side opening, and
    said tube further including a detent formed in said interior wall proximal said tab member where said tab member abuts said side wall.

2. A needle according to claim 1 wherein the width of said tab is substantially equal to the width of said side opening.

3. A needle according to claim 1 wherein the width of said side opening is less than the diameter of said lumen.

4. A needle according to claim 1 wherein said lumen extends into said tip.

5. A needle comprising:
a tube having a longitudinal axis and forming a lumen therethrough along said longitudinal axis, said tube forming a rotationally symmetrical tip at a distal end thereof and including a generally rectangular side opening adjacent said tip which extends into said lumen,
said tube further including a detent positioned in a side wall of said lumen directly opposite said side opening, said detent extending into said lumen at least a distance equal to the thickness of said side wall of said tube.

6. A method of manufacturing a needle including the steps of forming a tube having a lumen entirely therethrough,
forming a distal end of the tube into a rotationally symmetrical blunt tip,
cutting two longitudinal sides of an opening parallel to each other at a position proximal of and adjacent to the distal tip,
cutting a proximal side connecting the two parallel sides thus forming a tab of generally rectangular shape,
bending the tab into the lumen of the tube until it abuts with the interior wall of the lumen, and
forming a detent in the tube which extends into the lumen, the detent being formed directly proximally of the position of abutment of the tab against the interior wall of the lumen.

7. The method of claim 6 wherein the step of forming a blunt tip includes the step of swagging the distal end of the tube.

8. A method of forming a needle including the steps of:
forming a tube having a lumen therethrough,
forming a rotationally symmetrical blunt tip at a distal end of the tube,
forming a generally rectangular opening in the tube adjacent the tip, the opening extending into the lumen of the tube, and
forming a detent in the tube which extends into the lumen at a position on the interior wall of the lumen directly opposite the generally rectangular opening.

* * * * *